United States Patent [19]

Zohler

[11] Patent Number: 4,914,810

[45] Date of Patent: Apr. 10, 1990

[54] APPARATUS FOR MEASURING THE PORE SIZE OF ENHANCED TUBES

[75] Inventor: Steven R. Zohler, Manlius, N.Y.

[73] Assignee: Carrier Corporation, Syracuse, N.Y.

[21] Appl. No.: 803,378

[22] Filed: Dec. 2, 1985

[51] Int. Cl.⁴ ............................................. B21D 53/02
[52] U.S. Cl. ......................................... 73/38; 29/407;
  29/705; 29/720; 73/40; 73/49.1
[58] Field of Search ............... 29/157.3 R, 157.4, 407,
  29/703, 705, 714, 726, 709, 720; 73/168, 38,
  37.5, 40, 49.1

[56] References Cited

U.S. PATENT DOCUMENTS 2,703,978  3/1955  Baxter .
3,371,521  3/1968  Hauk .
3,871,209  3/1975  Hasha .

OTHER PUBLICATIONS

Kirk—Othmer, *encyclopedia of Chemical Technology*, second completely revised edition, vol. 21, pp. 97–99, John Wiley & Sons, Inc., 1970.

Primary Examiner—Howard N. Goldberg
Assistant Examiner—I. Cuda
Attorney, Agent, or Firm—Robert H. Kelly

[57] ABSTRACT

An apparatus for measuring the surface pore size in an externally enhanced evaporator tube. Basically, the apparatus includes a pressure housing and gage that are sealingly engagable around a portion of the surface of the enhanced tube, so that fluid pressure flows into the housing and then through the pores and subsurface channels on the tube and then to the outside of the housing. The pressure drop across the pores and subsurface channels of the tube relates to the size of the pores.

3 Claims, 2 Drawing Sheets

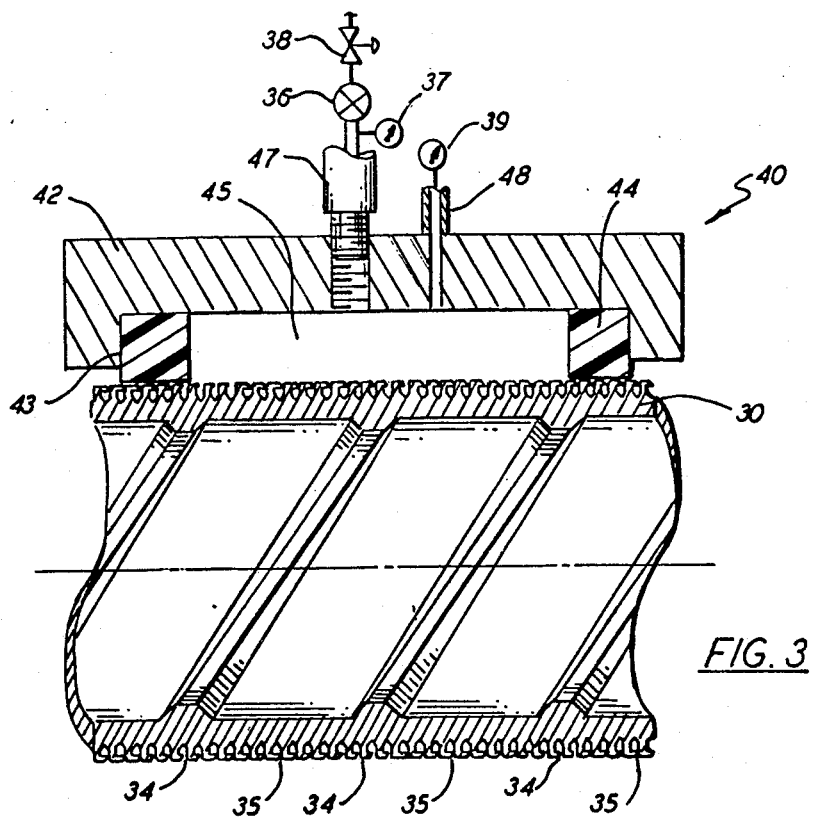
FIG. 3
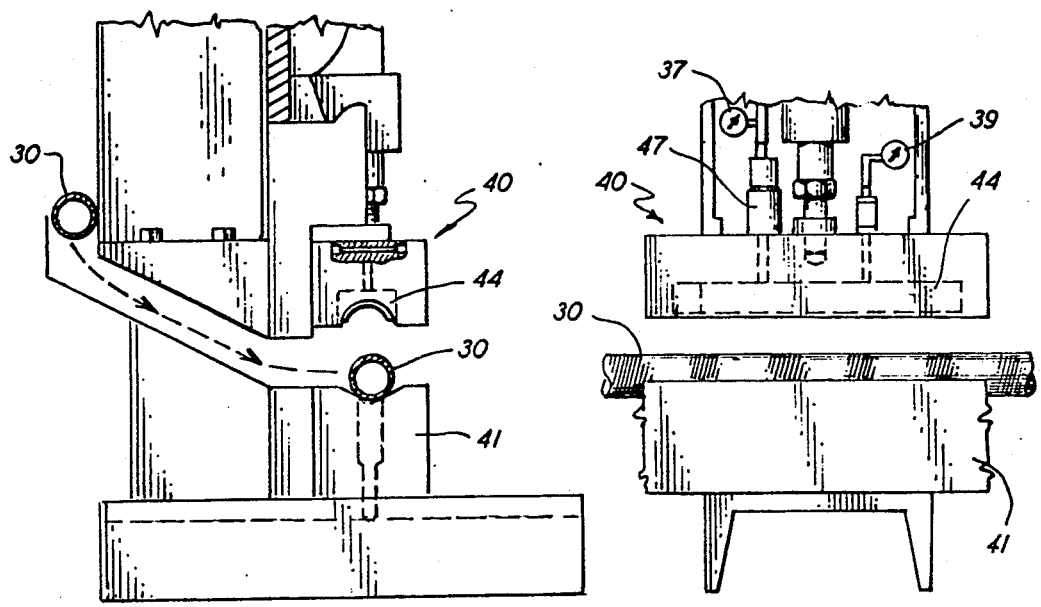
FIG. 4
FIG. 5

APPARATUS FOR MEASURING THE PORE SIZE OF ENHANCED TUBES

BACKGROUND OF THE INVENTION

This invention relates generally to measuring devices and more particularly to an apparatus for measuring the pore size in an externally enhanced evaporator tube having subsurface channels.

In the evaporator of certain refrigeration systems a fluid to be cooled is passed through heat transfer tubing while refrigerant in contact with the exterior of the tubing changes state from a liquid to a vapor by absorbing heat from the fluid within the tubing. The external and internal configuration of the tubing is important in determining the overall heat transfer characteristics of the tubing. For example, it is known that one of the most effective ways of transferring heat from the fluid within the tube to the refrigerant surrounding the tube is through the mechanism of nucleate boiling.

It is theorized that the provision of vapor entrapment sites or cavities cause nucleate boiling. According to this theory the trapped vapor forms the nucleus of a bubble, at or slightly above the saturation temperature, and the bubble increases in volume as heat is added until surface tension is overcome and a vapor bubble breaks free from the heat transfer surface. As the vapor bubble leaves the heat transfer surface, liquid refrigerant enters the vacated volume trapping the remaining vapor and another vapor bubble is formed. The continual bubble formation together with the forced convection effect of the bubbles traveling through and mixing with the boundary layer of superheated liquid refrigerant which covers the vapor entrapment site results in improved heat transfer. U.S. Pat. No. 3,301,314 discloses a heat exchange surface having a number of discrete artificial nucleation sites.

It is further known that a vapor entrapment site produces stable bubble columns when it is of the re-entrant type. In this context, a re-entrant entrapment site is defined as a cavity or groove in which the size of the surface pore or gap is smaller than the subsurface cavity or subsurface groove. U.S. Pat. Nos. 3,696,861 and 3,768,290 disclose heat transfer tubes having such re-entrant shaped grooves.

Also, it is known that an excessive influx of liquid from the surroundings can flood or deactivate a vapor entrapment site. In this regard, a heat transfer surface having subsurface channels communicating with the surroundings through surface openings having a specified "opening ratio" may provide good heat transfer and prevent flooding of the vapor entrapment site.

In regard to the interior surface configuration of a heat transfer tube it is known that providing an internal rib on the tube may enhance the heat transfer characteristics of the tube due to the increased turbulence of the fluid flowing through the ribbed tube.

As disclosed in U.S. Pat. Nos. 4,425,696 and 4,438,807 assigned to the present assignee, and incorporated by reference herein, an internally and externally enhanced heat transfer tube having an internal rib and an external subsurface channel communicating with the surrounding liquid through surface openings or pores may be manufactured by a single pass process with a tube finning machine. According to the disclosed process a grooved mandrel is placed inside an unformed tube and a tool arbor having a tool gang thereon is rolled over the external surface of the tube. The unformed tube is pressed against the mandrel to form at least one internal rib on the internal surface of the tube. Simultaneously, at least one external fin convolution is formed on the external surface of the tube by the tool arbor with the tool gang. The external fin convolution has depressed sections above the internal rib where the tube is forces into the grooves of the mandrel to form the rib. A smooth roller-like disc on the tool arbor is rolled over the external surface of the tube after the external fin is formed. The smooth roller-like disc is designed to bend over the tip portion of the external fin to touch the adjacent fin convolution to form subsurface channels only at those sections of the external fin which are not located above the internal rib. The tip portion of the depressed sections of the external fin, which are located above an internal rib, are bent over but do not touch the adjacent convolutions thereby leaving pores which provide fluid communication between the liquid surrounding of the tube and the subsurface channels.

The performance of the foregoing tube is critically dependent on the size of the subsurface channels and the size of the pores on the surface of the tube. It is therefore important to maintain a consistent subsurface channel size and surface pore size during the manufacturing process. Normal variations in subsurface channel size do occur, however, due to tool wear, dimensional and material variations in the tube lengths, and machine tolerances. In order to account for these variables and to maintain a consistent pore size, it is necessary to measure the pore size on each tube produced and adjust the finning machine to maintain the correct subsurface channel and pore sizes. However, the prior methods of having an operator randomly select manufactured tubes and optically checking the pore size of the selected tube under a microscope or taking a micro-photograph and comparing the area of the pores in a known area by image analysing, was time consuming and did not provide the quality and quantity of tubes necessary for a manufacturing process. Not only is this a very laborious and expensive practice, but it also cannot check each and every tube in a manufacturing process.

Thus, there is a clear need for an apparatus for measuring the size of the surface pores in an enhanced tube that will, to a large extent, overcome the inadequacies that have characterized the prior art.

SUMMARY OF THE INVENTION

An enhanced tube pore size measuring device in accordance with the principles of the present invention is characterized by a measuring device having a sealed chamber in contact with the enhanced tube surface, whereby compressed air flows into the chamber and into the pores on the surface of the enhanced tube and through the subsurface channels in the tube and out an outlet pore to the surroundings resulting in a pressure drop across the chamber, thus giving a measurment of the average size of the surface pores on the enhanced tube. The air pressure drop across the surface pores on the tube correlates to the size of the subsurface channels and pores, and thus correlates to the expected boiling heat transfer coefficient of the tube.

Accordingly, it is an object of the present invention to provide a system which measures average subsurface channel and pore size on an enhanced tube surface.

Another object of the present invention is to provide a measurement system which can inspect 100% of the enhanced tubes that are produced.

A further object of the present invention is to provide a measurement system which measures the average subsurface channel size and pore size on each tube produced and allows adjustment of the finning machine to maintain the correct surface enhancement.

These and other objects of the present invention are attained by a measurement system comprising a test block having a sealing means matingly engagable around a particular surface area of the enhanced tube. The test block, sealing means, and particular surface area form a sealed chamber defining a flow path through which compressed dry air is blown into the chamber and through the pores and subsurface channels of the enhanced tube whereby the resulting difference in pressure between the inlet and outlet of the chamber corresponds to the area through which the air can leak from the chamber. This corresponding area is a measurement of the sum of all the individual pore areas for that segment on the enhanced tube which lies beneath the plane surface area projection of the chamber.

Thus, the invention measures the average pore size of an enhanced tube and allows adjustment of the finning machine to maintain the correct pore size.

The various features of novelty which characterize the invention are pointed out with particularity in the claims annexed to and forming a part of this specification. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWINGS

Other objects and advantages of the present invention will be apparent from the following detailed description in conjunction with the accompanying drawings, forming a part of this specification, and in which reference numerals shown in the drawings designate like or corresponding parts throughout the same, and in which;

FIG. 3 is a vertical section of a part of an enhanced tube incorporating the pore measuring device in accordance with the present invention;

FIG. 4 is a transverse elevational view of the pore measuring device of the present invention; and FIG. 5 is a front elevational view of the pore measuring device shown in FIG. 4.

DESCRIPTION OF THE PREFERRED EMBODIMENT

The embodiment of the present invention described below is especially designed for use with enhanced evaporator tubes because these tubes have a critical dimension which must be precisely controlled to maintain good heat transfer performance. These enhanced tubes are designed for use in an evaporator of a refrigeration system having a fluid to be cooled passing through heat transfer tubes and having refrigerant, which is vaporized, in contact with the external surfaces of the tubes. Typically, a plurality of heat transfer tubes are mounted in parallel and connected so that several tubes form a fluid flow circuit and a plurality of such parallel circuits are provided to form a tube bundle. Usually, all of the tubes of the various circuits are contained within a single shell wherein they are immersed in the refrigerant. The heat transfer capability of the evaporator is largely determined by the average heat transfer characteristics of the individual heat transfer tubes. The size of the subsurface channels and pores on the surface of the tubes are particularly critical for R-11 applications. Therefore, it is important to maintain a consistent pore size during the manufacturing process of enhanced evaporator tubes.

Figure 1:
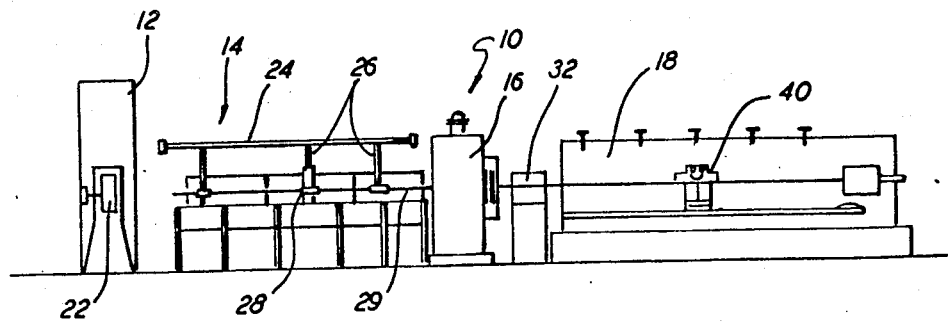
FIG. 1 is a schematic representation of a finning machine for the manufacture of enhanced tubes in accordance with the present invention.

Referring now to the drawings, FIG. 1 is a diagrammatic representation of a finning station for manufacturing enhanced tubes used in connection with the present invention. The finning station 10 includes an electronic control cabinet 12, a feed section 14, a finning head section 16, an ejection section 32 and a pore measurement section 18. The electronic control cabinet includes a programmable controller and an operator console 22 which perform logic execution, timing, sequencing, and calculations for the finning operation. The feed section 14 generally includes two similar parallel mandrels 24 (the rearward mandrel is in the horizontal plane of the forward mandrel and thus is not shown in the Figure) typically supported by a plurality of support arms 26 and positioned by piston means 28. Accordingly, the operator will load a blank tube on the front and rear mandrels 24 and cycle the feed section 14 such that one mandrel, e.g. the front mandrel, will drop down and move the blank tube along the longitudinal finning axis 29 into the finning head section 16. The finning head section 16 includes an arrangement of a plurality of tool arbors with tool gangs thereon. The tool gangs having a plurality of finning discs and rollers cooperating with the mandrel, as is well known in the art, to produce the enhanced tube. The finning process inherently moves the enhanced tube by action of the finning discs, through the finning head section 16 to the ejection section 32. When the blank tube is completely enhanced the tool arbors of the finning head section 16 will open and the mandrel will retract to its original position while ejection means, e.g. eject wheels, in the ejection section 32 will engage the enhanced tube and send it into the pore measurement section 18. Once the enhanced tube is completely into the pore measurement section 18 the rear mandrel 24 will now drop down and the process will repeat itself.

Figure 2:
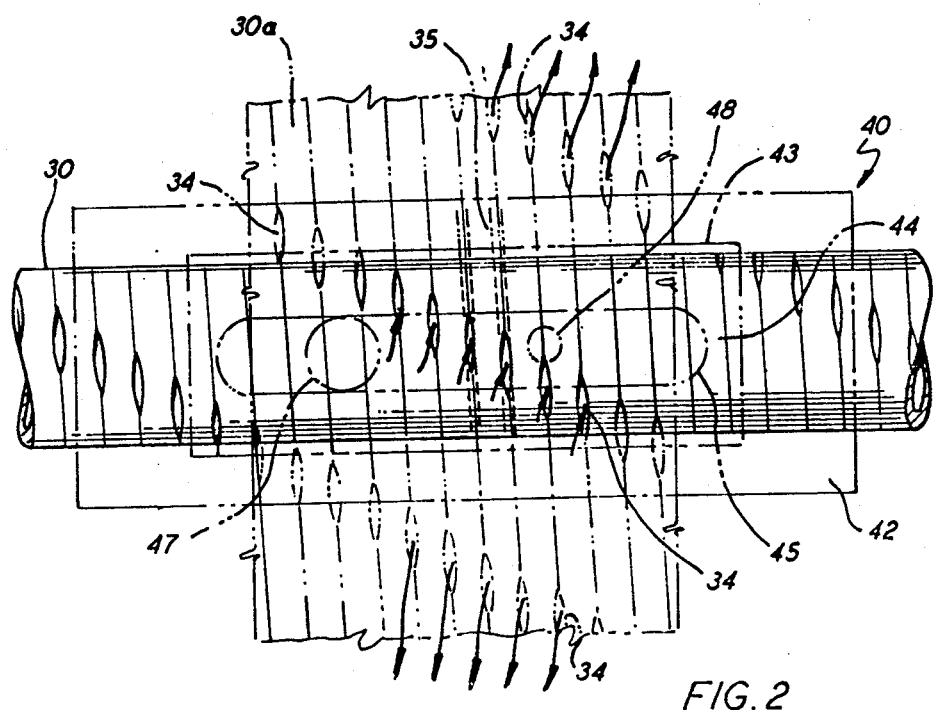
FIG. 2 is a magnified view of the exterior surface of the enhanced tube manufactured by the finning machine shown in FIG. 1 with the pore measuring device of the present invention mating therewith, and further with a portion of the tube, showing in phantom, projected into a flat plane.

In FIGS. 2-5, the pore measurement section 18 is more completely described. As shown in FIG. 2, the pore measuring tool 40, which comprises a generally rectangular block 42 having a slot 43 provided therein for the receipt of flexible insert 44, e.g. moldable urethan, with a chamber 45 therein, matingly engages with a portion of the surface of the enhanced tube 30. An air inlet 47 and air outlet 48 extend through the rectangular block 42 to the chamber 45.

Also, FIGS. 2 and 3 show an enhanced tube 30 consisting of subsurface channels 35 communicating with the surroundings of the tube through the pores 34. The rectangular block 42 and flexible insert 44 have an arcuate longitudinal channel therein whereby the flexible insert matingly engages with the surface of the enhanced tube 30. The flexible insert 44 acts like a gasket against the surface of the enhanced tube. Thus, as clearly shown in FIG. 2 (wherein the enhanced tube is shown in a flattened position 30(a) and the normal tube position 30), when air is blown into chamber 45 through inlet 47, having the flexible insert 44 sealed against the surface of the enhanced tube, the air in chamber 45 must either enter pores 34 in the surface of the tube within the projected area of the chamber 45 and flow through corresponding subsurface channels 35 and out pores 34 outside the projected area of the chamber to the surroundings, as shown by the arrows or remain in the chamber 45 whereby it can be read on pressure gage 39 secured to air outlet 48.

FIGS. 4 and 5 show an enhanced tube 30 supported in a channel support 41 below the pore measuring tool 40. The air inlet 47 is supplied with constant pressure air by regulator 38. The air pressure at outlet 48 is measured by pressure gage or manometer 39. With the enhanced tube in the channel support 41, the measuring tool 40 is lowered, by a known method, so that the flexible insert 44 matingly engages with the surface of the tube as shown in FIG. 3. Accordingly, during operation, with constant pressure air flowing through regulator 38 a portion of the pressure is lost across flow control valve 36 in the flow path and read on gage 37. The remainder of the pressure, not lost across the surface pores 34 is read on gage 39. Thus, the difference between the pressure on gage 37 and gage 39 gives the pressure drop across the pores which is a measure of the average pore size on the tube. This average pore size measurement can be determined by measuring the boiling heat transfer coefficient of tubes having a known pressure drop across their pores and determining the optimum pore size. A correlation can thus be established between the pressure drop across pores and the expected boiling hat transfer coefficient.

The theory involved in this invention is that the pressure drop across an orifice is a function of the area of the orifice. If an enhanced tube with pores leading to subsurface channels on the surface has compressed air blown through the pores, the resulting pressure drop gives a measure of the average size of the pores on the enhanced tube. The pressure drop across the pores of the tubes correlate to the expected boiling heat transfer coefficient of the tube.

In operation, an enhanced tube comprising a continuous subsurface channel with a closed surface having pores spaced along the closed surface, is engaged by a pore size measuring device comprising a generally rectangular fixture having a passageway therein in which a flexible sealing means having a chamber therein is secured. The chamber has an inlet through which air from an air source, is blown and an outlet pressure tap. A manometer is connected to the outlet pressure tap to read the pressure in the chamber. Accordingly, the pressure at the manometer is equal to the inlet pressure minus the air pressure that is lost across the pores and subsurface channels of the tube.

Of course, the foregoing description of an apparatus for measuring the pore size in an enhanced tube is directed to a preferred embodiment, and various modifications and other embodiments of the present invention will be readily apparent to one of ordinary skill in the art to which the present invention pertains. Therefore, while the present invention has been described in conjunction with a particular embodiment it is to be understood that various modifications and other embodiments of the present invention may be made without departing from the scope of the invention as described herein and as claimed in the appended claims.

What is claimed is:

1. A device for determining the average pore size on a portion of a circumferential section of the exterior surface of an enhanced tube having subsurface channels connected by pores on the exterior surface, comprising:
    a support member for supporting a section of the exterior surface of the enhanced tube therein;
    at least one body member having a single longitudinal recess in said body member aligned axially of said enhanced tube;
    a sealing member connected to said body member, said sealing member sealingly engageable around the portion of the circumferential section of the exterior surface of the enhanced tube; and
    a compressed air fluid pressure source connected to said recess to that a constant fluid pressure is maintained at an inlet to said recess whereby the fluid pressure is discharged for said recess through the pores on the exterior surface of the enhanced tube and through the connected subsurface channels to the surroundings outside the body member.

2. An device as set forth in claim 1 wherein said sealing means is moldable urethan.

3. A device as set forth in claim 1 wherein said sealing member is a moldable plastic material.

* * * * *